(12) United States Patent
Kushlin et al.

(10) Patent No.: US 9,757,227 B2
(45) Date of Patent: Sep. 12, 2017

(54) INTRAOCULAR ASSEMBLY

(71) Applicant: HANITA LENSES R.C.A. LTD., Kibbutz, Hanita (IL)

(72) Inventors: Yakir Kushlin, Haifa (IL); Alex Maliarov, Akko (IL); Guy Kleinmann, Rehovot (IL)

(73) Assignee: HANITA LENSES, Kibbuts Hanita (IL)

( * ) Notice: Subject to any disclaimer, the term of this patent is extended or adjusted under 35 U.S.C. 154(b) by 0 days.

(21) Appl. No.: 14/395,551

(22) PCT Filed: Apr. 19, 2013

(86) PCT No.: PCT/US2013/037267
§ 371 (c)(1),
(2) Date: Oct. 20, 2014

(87) PCT Pub. No.: WO2013/158942
PCT Pub. Date: Oct. 24, 2013

(65) Prior Publication Data
US 2015/0157452 A1     Jun. 11, 2015

Related U.S. Application Data

(60) Provisional application No. 61/635,882, filed on Apr. 20, 2012.

(51) Int. Cl.
*A61F 2/16* (2006.01)

(52) U.S. Cl.
CPC .............. *A61F 2/16* (2013.01); *A61F 2/1648* (2013.01); *A61F 2/1694* (2013.01); *A61F 2002/16901* (2015.04); *A61F 2002/16902* (2015.04)

(58) Field of Classification Search
CPC .. A61F 2/16; A61F 2002/1681; A61F 2/1648; A61F 2002/16901; A61F 2/147;
(Continued)

(56) References Cited

U.S. PATENT DOCUMENTS 6,063,118 A     5/2000  Nagamoto
6,136,026 A *  10/2000  Israel ........................ A61F 2/16
                                                          623/6.11
(Continued)

FOREIGN PATENT DOCUMENTS

EP     1743601      1/2007
WO    01/64136      9/2001
(Continued)

OTHER PUBLICATIONS

PCT Written Opinion and Search PCT/US2013/037267, Sep. 18, 2013.
Rosen et al., "In vitro dimensions and curvatures of human lenses", Vision Research 46 (2006) 1002-1009 (8 pages).

*Primary Examiner* — Paul Prebilic
(74) *Attorney, Agent, or Firm* — Roach Brown McCarthy & Gruber, P.C.; Kevin D. McCarthy

(57) ABSTRACT

An intraocular assembly includes a peripheral side wall (12) that has a rim (16) sized to receive therein an intraocular device, and a posterior peripheral edge (20) that is sharp and extends out from a posteriorly-facing end face (22) of the side wall. An interior perimeter of the rim is a combination of continuous concave and convex shapes.

17 Claims, 2 Drawing Sheets

(58) Field of Classification Search
CPC ............ A61F 2/16015; A61F 2002/169; A61F 2002/16902; A61F 2220/0025; A61F 2220/0033; A61F 2230/0065; A61F 2230/0095; A61F 2250/005; A61F 2250/006–2250/0063; A61F 2250/0091
See application file for complete search history.

(56) References Cited

U.S. PATENT DOCUMENTS

| | | | | |
|---|---|---|---|---|
| 6,558,419 | B1 * | 5/2003 | Pham | A61F 2/1613 623/4.1 |
| 6,749,634 | B2 * | 6/2004 | Hanna | A61F 2/1613 623/6.37 |
| 6,797,004 | B1 * | 9/2004 | Brady | A61F 2/1648 623/6.38 |
| 6,926,736 | B2 * | 8/2005 | Peng | A61F 2/1613 623/6.34 |
| 8,900,300 | B1 * | 12/2014 | Wortz | A61F 2/1648 623/6.38 |
| 2003/0050695 | A1 * | 3/2003 | Lin | A61F 2/1613 623/6.37 |
| 2003/0130732 | A1 * | 7/2003 | Sarfarazi | A61F 2/1648 623/6.13 |
| 2003/0144733 | A1 * | 7/2003 | Brady | A61F 2/1613 623/6.16 |
| 2006/0047339 | A1 * | 3/2006 | Brown | A61F 2/1602 623/6.13 |
| 2006/0142855 | A1 * | 6/2006 | Vaudant | A61F 2/1616 623/6.16 |
| 2009/0005864 | A1 | 1/2009 | Eggleston | |
| 2011/0040379 | A1 * | 2/2011 | Bumbalough | A61F 2/1613 623/6.43 |

FOREIGN PATENT DOCUMENTS

| | | |
|---|---|---|
| WO | 01/66042 | 9/2001 |
| WO | 2007/082342 | 7/2007 |

* cited by examiner

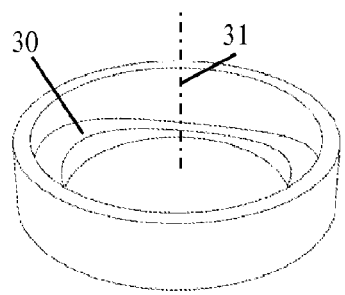
FIG. 4A
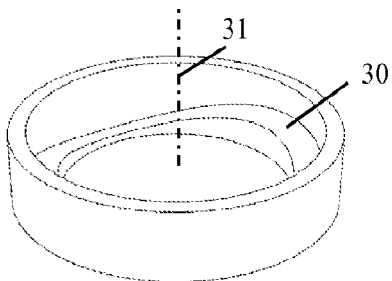
FIG. 4B
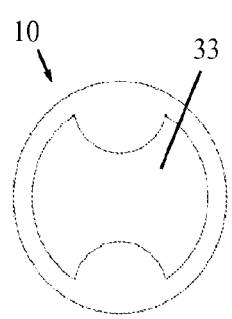
FIG. 5
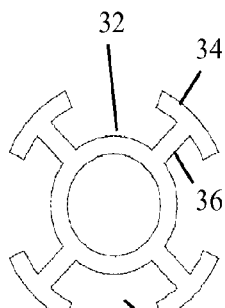
FIG. 6
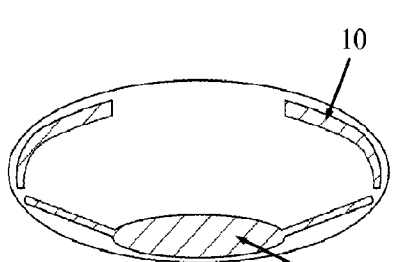
FIG. 7
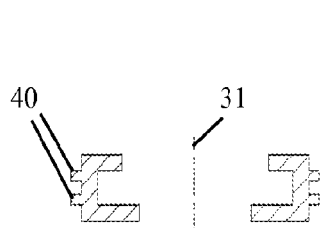
FIG. 8A  FIG. 8B  
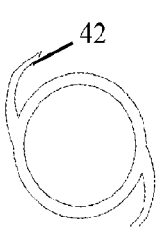
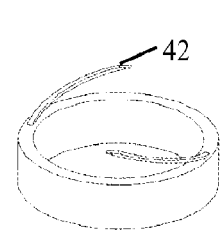
FIG. 8C
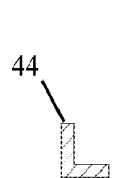
FIG. 8D
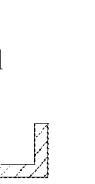
FIG. 8E
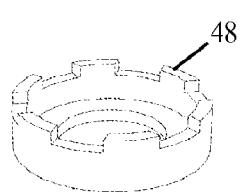
FIG. 8F
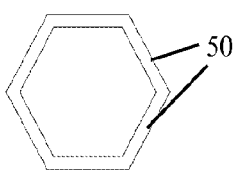
FIG. 8G

INTRAOCULAR ASSEMBLY

CROSS REFERENCE TO OTHER APPLICATIONS

This application is a US national phase application of PCT patent application PCT/US2013/037267, filed Apr. 19, 2013, which claims priority from U.S. Provisional Patent Application 61/635,882, filed Apr. 20, 2012.

FIELD OF THE INVENTION

The present invention relates to cataract surgery implants and side effects and particularly to an intraocular assembly, which helps prevent posterior capsule opacification (PCO) and posterior vitreous detachment (PVD), such as an assembly for mounting therein an intraocular lens (IOL), which also helps prevent IOL displacement.

BACKGROUND OF THE INVENTION

With age, a human crystalline lens opacifies (cataract) disabling the eye in generating a clear, well contrasted image. The only therapeutic solution to this problem is surgical replacement of the crystalline lens with an artificial intraocular lens (IOL). An IOL typically has two major components, a central lens or optic, and haptics. The IOL can be made of relatively rigid materials, such as polymethylmethacrylate (PMMA) or soft materials for foldable IOLs, such as silicone, soft acrylics, hydrogels and others.

The natural lens is removed from the capsular bag prior to insertion of the IOL. However, there are always residual lens epithelial cells (LECs) which remain attached to the remaining portions of the anterior capsule and to the equatorial portions of the lens capsule at the conclusion of the surgical procedure. These remaining LECs reproduce and migrate across the posterior capsule and undergo lens fiber regeneration and epithelial-to-mesenchymal transition. This shows up as a thickening, opacification and clouding of the posterior lens capsule, which may compromise visual acuity.

In addition, opacification of the anterior lens capsule can occur. This may lead to contraction of the capsulorhexis opening, and in extreme cases to phimosis. In cases of asymmetric or phimotic contraction, the IOL might move along the optical axis, causing change in refraction or causing a decrease in visual acuity.

As an additional side effect of the cataract surgery, a posterior vitreous detachment (PVD) might occur. PVD is a condition of the eye in which the vitreous gel separates from the retina. Although this does not directly threaten vision, the interaction between the vitreous body and the retina might play a decisive role in the development of major pathologic vitreoretinal conditions.

SUMMARY OF THE INVENTION

The present invention seeks to provide an intraocular assembly, which helps prevent posterior capsule opacification (PCO) and posterior vitreous detachment (PVD), such as an assembly for mounting therein an intraocular lens (IOL), which also helps prevent IOL displacement, as is explained more in detail further below.

In one embodiment, the IOL is held in the middle of the assembly spaced from the anterior capsule and the posterior capsule. The assembly has sharp edges to help prevent PCO.

BRIEF DESCRIPTION OF THE DRAWINGS

These and additional constructional features and advantages of the invention will be more readily understood in the light of the ensuing description of embodiments thereof, given by way of example only, with reference to the accompanying drawing wherein:

FIGS. 4A-4B are simplified illustrations of an alternative mounting of the intraocular assembly, which has an inner inclined ramp, in accordance with an embodiment of the present invention;

FIG. 5 is a simplified illustration of an intraocular assembly, in which an interior perimeter of the rim is a combination of continuous concave and convex shapes, in accordance with an embodiment of the present invention;

FIG. 6 is a simplified illustration of an intraocular assembly, in which an outer rim is connected to an inner rim with ribs, in accordance with an embodiment of the present invention;

FIG. 7 is a simplified illustration of an intraocular assembly, in which the IOL is not supported by or mounted in the intraocular assembly, in accordance with an embodiment of the present invention; and FIGS. 8A-8G are simplified illustrations of intraocular assemblies, constructed and operative in accordance with different embodiments of the invention.

DETAILED DESCRIPTION OF EMBODIMENTS

Figure 1:
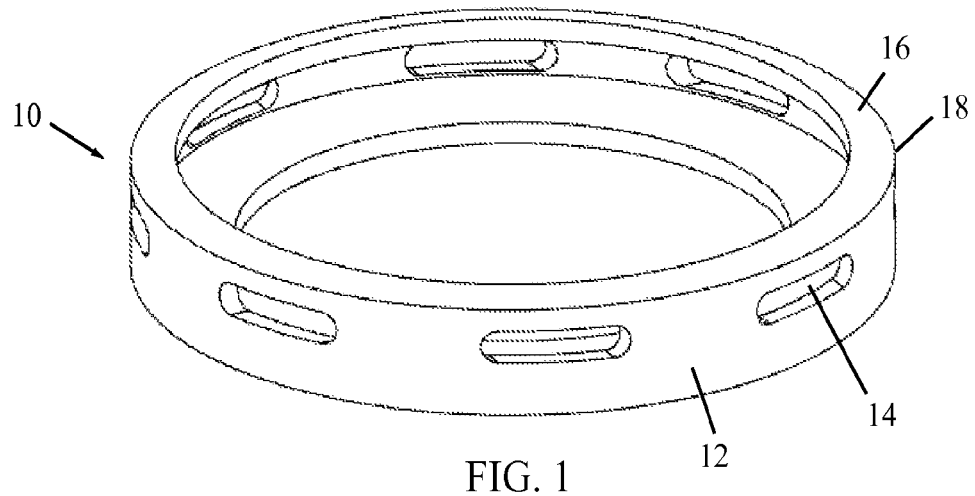
FIG. 1 is a simplified perspective illustration of an intraocular assembly, constructed and operative in accordance with an embodiment of the present invention.
Figure 2:
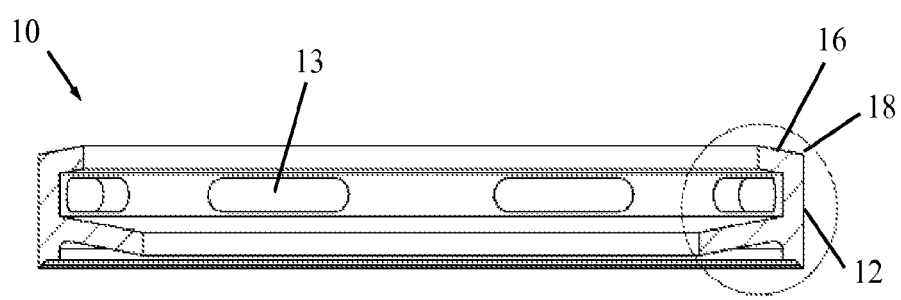
FIG. 2 is a simplified, partially sectional, side-view illustration of the intraocular assembly of FIG. 1.
Figure 3:
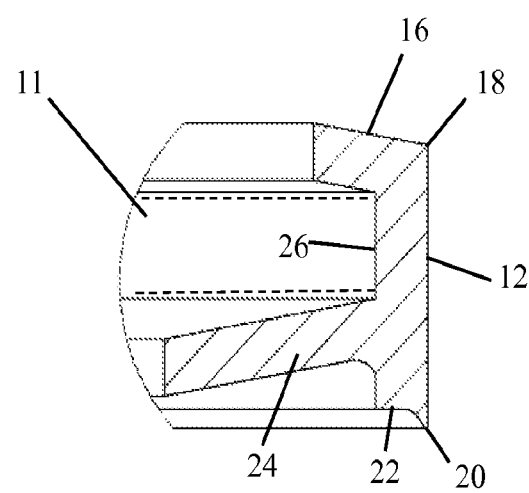
FIG. 3 is an enlarged illustration of a peripheral edge of the intraocular assembly of Fig. of FIG. 2.

Reference is now made to FIGS. 1-3, which illustrate an intraocular assembly 10, constructed and operative in accordance with a non-limiting embodiment of the present invention.

Intraocular assembly 10, in the illustrated embodiment, includes a ring with a generally circular side wall 12 in which a plurality of apertures 14 are formed. One purpose of the apertures 14 is to allow for fluid to flow through. Optionally, haptics (not shown) of an IOL 11 (partially shown in broken lines in FIG. 3) can pass through apertures 14, particularly if the intraocular assembly 10 is smaller than the capsule (or a little larger than the IOL optic). Any of the apertures 14 can have a shutter 13 (FIG. 2) so that the aperture can be closed or opened.

Alternatively, side wall 12 does not have to be circular and can have any arbitrary shape (examples of which are shown in FIGS. 5 and 6).

It is noted that IOL 11 encompasses not only a solid lens, but also any kind of transparent filling (liquid, gel or solid) or any intraocular device (not necessarily a lens).

Intraocular assembly 10 has an anterior rim 16 that extends radially inward at an acute angle, anteriorly outwards from an anterior edge 18 of side wall 12. One of the purposes of the outwardly-angled rim 16 is to help expand the capsular bag, after the IOL and intraocular assembly 10 have been inserted, which helps distance the IOL and intraocular assembly 10 from any residual lens epithelial cells (LECs) which remain attached to the remaining portions of the anterior capsule.

A posterior peripheral edge 20 of intraocular assembly 10 is sharp to help prevent PCO. The sharp posterior peripheral edge 20 flares out from a posteriorly-facing end face 22 of side wall 12.

A posterior rim 24 extends radially inward at an acute angle in a posterior direction from an inner perimeter of side wall 12. There is a gap 26 on the inner perimeter of side wall 12 between anterior rim 16 and posterior rim 24, in which sits the outer perimeter of IOL 11 (FIG. 3). The posterior rim 24 is radially larger than anterior rim 16. This may help prevent the haptics of the IOL from inadvertently extending towards the posterior part of the bag. The innermost extremity of posterior rim 24 is not coplanar with (i.e., does not reach the same plane of) end face 22 of side wall 12, as seen in FIG. 3. However, optionally the innermost extremity of posterior rim 24 can be coplanar with end face 22.

Intraocular assembly 10 is preferably constructed of a clear, transparent, biologically compatible material, such as but not limited to, polymethylmethacrylate (PMMA), silicone, silicone rubber, collagen, hyaluronic acid (including the sodium, potassium and other salts thereof), hydrogel, such as acrylic or methacrylic hydrogels, e.g., hydroxyethyl methacrylate or methacrylic acid copolymer/partially hydrolyzed poly(2-hydroxyethyl methacrylate) (known as Poly-HEMA), polysulfones, thermolabile materials and other relatively hard or relatively soft and flexible biologically inert optical materials, or any combination of such materials. Intraocular assembly 10 may thus be rigid, semi-rigid or foldable, for example.

Intraocular assembly 10 helps prevent PCO in several ways. IOL 11 is held in the middle of the intraocular assembly 10, spaced from the anterior capsule and the posterior capsule, distanced from the LECs. Intraocular assembly 10 has sharp edges to help prevent PCO. Intraocular assembly 10 fills out the capsular bag, perhaps lowering the urge of the body to fill the empty space and allowing the flux of the anterior chamber liquids, suggested being toxic to the LECs. In addition, refilling the capsular bag gets the eye closer to the pre-operative state, minimizing the deviation from equilibrium of the vitreous gel, which in turn may help in prevention of PVD occurring after the cataract surgery.

Any or all of the above features may be incorporated in any of the embodiments described throughout the disclosure.

As mentioned above, the IOL may be mounted in gap 26 between anterior rim 16 and posterior rim 24. Reference is now made to FIGS. 4A-4B, which illustrate an alternative mounting, in which the rim (either anterior or posterior or both) or any other inner portion of the side wall is formed with an inner inclined ramp 30, such as a saddle shape or a screw thread. In this manner, the IOL can be mounted in the intraocular assembly and rotated to change the axial position of the IOL along the anterior-posterior axis 31 of the assembly. This enables the surgeon to modify the IOL power in the eye by means of IOL rotation. The anterior and posterior rims can be of any thickness, size and shape.

The intraocular assembly 10 may be made of colored plastic, allowing visibility of proper IOL haptic location.

An alternative, non-circular shape of the intraocular assembly 10 is shown in FIG. 5, in which an interior perimeter 33 of the rim (anterior or posterior or both) is a combination of continuous concave and convex shapes. The inner diameter of the posterior rim can be small (e.g., less than 6 mm) so that the iris does not block the surgeon's field of view, making the implantation easier. Another shape is shown in FIG. 6, in which the intraocular assembly has an inner rim 32 and an outer rim 34 connected to the inner rim 32 with ribs 36. Outer rim 34 is not continuous but instead has gaps 38.

In another alternative, shown in FIG. 7, the IOL 11 is not supported by or mounted in intraocular assembly 10. Instead, the IOL 11 is mounted by itself in the posterior side of the capsule, while the intraocular assembly 10 independently maintains the capsule open.

The intraocular assembly may have outer ribs 40 extending from the peripheral side wall for reinforcement (FIG. 8A), or haptics 42 for fitting to different capsular sizes (FIG. 8B) or for urging the assembly to a predetermined direction (FIG. 8C). The intraocular assembly can be devoid of an anterior rim and only have a posterior rim 44 (FIG. 8D). The intraocular assembly can have one or more sharp edges 46 on both sides (FIG. 8E). The intraocular assembly may have a crown shape 48 (FIG. 8F). The intraocular assembly may have a periphery constructed of bendable slats 50 (FIG. 8G), which can be bent, folded or straightened to obtain different heights, widths and shapes.

The invention includes further embodiments which are combinations of any or all of the embodiments described above. For example, the embodiment of FIGS. 4A-4B can be combined with the embodiment of FIG. 5, and so forth.

What is claimed is:

1. An intraocular assembly comprising:
a ring sized and shaped to fill a capsular bag of a human eye, said ring having a peripheral side wall that has:
a posterior rim and an anterior rim both extending from an inner perimeter of said peripheral side wall towards a center of said ring, wherein a gap between said posterior rim and said anterior rim is sized to receive therein an intraocular lens, and
two posterior peripheral edges that are sharp and flare out from a posteriorly-facing end face of said side wall, thereby preventing posterior capsule opacification, wherein one of said two posterior peripheral edges flares out from an outermost perimeter of said posteriorly-facing end face of said side wall.

2. The intraocular assembly according to claim 1, wherein at least one of said posterior and anterior rims is formed with an inner inclined ramp sized to receive therein the intraocular lens, wherein the inclination of said inner inclined ramp is along an anterior-posterior axis of said ring, and wherein rotation of the intraocular lens along said inclined ramp changes an axial position of the intraocular device along an anterior-posterior axis of said ring.

3. The intraocular assembly according to claim 1, wherein a plurality of apertures are formed in said side wall.

4. The intraocular assembly according to claim 1, wherein said anterior rim extends anteriorly outwards from the anterior edge of said side wall, and said posterior rim extends radially inward in a posterior direction from the inner perimeter of said side wall.

5. The intraocular assembly according to claim 1, wherein said posterior rim is radially larger than said anterior rim.

6. The intraocular assembly according to claim 1, wherein an innermost extremity of said posterior rim is not coplanar with a posteriorly-facing end face of said side wall.

7. The intraocular assembly according to claim 1, wherein said intraocular assembly is made of colored plastic.

8. The intraocular assembly according to claim 1, wherein at least one of said posterior and anterior rims comprises an inner rim and an outer rim connected to said inner rim with ribs.

9. The intraocular assembly according to claim 8, wherein said outer rim is not continuous.

10. The intraocular assembly according to claim 1, further comprising outer ribs that extend from said peripheral side wall.

11. The intraocular assembly according to claim 1, wherein said peripheral side wall comprises bendable slats.

12. The intraocular assembly according to claim 3, wherein any one of said apertures comprises a shutter so that the aperture can be closed or opened.

13. The intraocular assembly according to claim 2, wherein said inner inclined ramp is saddle-shaped.

14. The intraocular assembly according to claim 2, wherein said inner inclined ramp is shaped as a screw thread.

15. The intraocular assembly according to claim 1, further comprising at least one anterior peripheral edge that is sharp and flares out from an anteriorly-facing end face of said side wall, thereby further preventing posterior capsule opacification.

16. The intraocular assembly according to claim 15, wherein said at least one anterior peripheral edge is two anterior peripheral edges.

17. The intraocular assembly according to claim 2, wherein said inner inclined ramp comprises a combination of continuous concave and convex shapes.

* * * * *